United States Patent [19]

Erskine

[11] Patent Number: 4,897,082
[45] Date of Patent: Jan. 30, 1990

[54] APPARATUS FOR PROVIDING A SUTURE TAB

[75] Inventor: Timothy J. Erskine, Salt Lake City, Utah

[73] Assignee: Becton, Dickinson and Company, Franklin Lakes, N.J.

[21] Appl. No.: 325,610

[22] Filed: Mar. 20, 1989

[51] Int. Cl.⁴ .............................................. A61M 5/32
[52] U.S. Cl. ............................ 604/180; 128/DIG. 26; 604/177
[58] Field of Search .................................. D24/51, 54; 128/DIG. 26; 604/177, 180

[56] References Cited

U.S. PATENT DOCUMENTS

| | | | |
|---|---|---|---|
| 3,046,984 | 7/1962 | Eby | 604/180 |
| 3,046,989 | 7/1962 | Hill | 604/180 |
| 3,574,306 | 4/1971 | Alden | 604/162 |
| 3,630,195 | 12/1971 | Santomieri | 604/180 |
| 3,677,250 | 7/1972 | Thomas | 604/180 |
| 3,696,920 | 10/1972 | Lahay | 206/370 |
| 3,702,612 | 11/1972 | Schlesinger | 604/180 |
| 3,826,254 | 7/1974 | Mellor | 604/180 |
| 3,834,380 | 9/1974 | Boyd | 604/180 |
| 3,918,446 | 11/1975 | Buttaravoli | 604/180 |
| 3,973,565 | 8/1976 | Steer | 604/180 |
| 4,059,105 | 11/1977 | Cutruzzula et al. | 604/180 |
| 4,074,397 | 2/1978 | Rosin | 604/180 |
| 4,122,857 | 10/1978 | Haerr | 604/180 |
| 4,142,527 | 3/1979 | Garcia | 604/180 |
| 4,165,748 | 8/1979 | Johnson | 604/180 |
| 4,335,468 | 6/1982 | Geist | 604/180 |
| 4,583,976 | 4/1986 | Ferguson | 604/174 |
| 4,617,017 | 10/1986 | Hubbard et al. | 604/179 |

Primary Examiner—Edward M. Coven
Assistant Examiner—Gary Jackson
Attorney, Agent, or Firm—Aaron Passman

[57] ABSTRACT

A suture tab body has inside and outside surfaces and first and second parts with a line therebetween. Openings located about the first part pass through the body from the inside to the outside surface. Adhesion means on a section of the inside surface is juxtaposed to itself when the first and second parts are folded along the line. The openings in the first part are on another section apart from the adhesion means. A reinforcement as a thicker area of the first part has ears for the openings. The ears are adjacent a pair of opposite edges, each of which defines an elongate dimension of the body. And least two ears are disposed near each edge with one ear near each edge and the line. The adhesion means is a double faced foam tape with a releasable covering for protecting an adhesive facing prior to use. A combination of suture tab and catheter is used with a method for attaching the suture tab to the catheter. The method has the suture bab placed against the patient with the adhesive exposed to receive transversely the catheter. Folding the suture tab puts the outside surface of the second part away from the patient and so the inside surface carrying the adhesive is about the catheter and itself.

30 Claims, 2 Drawing Sheets

APPARATUS FOR PROVIDING A SUTURE TAB

Background of the Invention

1. Field of the Invention

This invention relates to an apparatus and method for attaching a tab to a catheter tube so that the tube can be secured by suturing to the patient and more specifically, to an apparatus and method for the permanent attachment of a suture tab to a catheter tube at any place along the tube are disclosed.

2. Background Description

In the treatment of patients, catheter tubes are inserted into the lumens of the vessels or arteries in order to infuse medication, monitor blood gases, flow or other physical characteristics of the patient's blood, or to remove samples for purposes of external testing. Peripheral lines are inserted in the limbs and are usually relatively short. However, longer catheter tubes are sometimes threaded from the limbs into the torso of the patient in order to provide a catheter in the lumen of choice. Similarly, long catheter tubes or lines are frequently positioned subclavian into the superior vena cava and other centrally located lumens. Such longer lines are typically made with sufficient length so that the tip of the catheter can be placed precisely at a site within the chosen lumen. This procedure is performed using a radiopaque catheter and x ray equipment thus permitting the practitioner to place the tip of the catheter at the preferred site.

Frequently, multilumen catheter tubes are used for simultaneously infusing several medications, simultaneously taking samples and infusing medication, or infusing a bolus and measuring thermodilution. These long multilumen catheters, which are centrally placed, are frequently used for total parenteral nutrition or chemotherapy and the patients which receive them are generally very ill. It is important that these life supporting and saving catheter lines be securely fastened to the patient in order that the life extending medications are continued without interruption.

In the past integral suturing ears have been molded as a part of the adapter which connects the multilumen catheter tube to its various extension tubes. This arrangement has been unsatisfactory because the ears provided are frequently located along the catheter tubing at a position which is remote from the puncture site where the multilumen catheter tube enters the patient's skin. Consequently, securing the multilumen catheter tube close to the entry site was not always feasible. It is appreciated that with longer catheter tubes the location of the integral or fixed suturing ears such as those molded to the adapter is not always an ideal relative to the desired site for placement of the tip of the catheter tube.

Suturing to secure the catheter tube is important in the treatment of the patients on long centrally placed catheter lines in that such patients are frequently on catheter tubing for several weeks or more. Consequently, all of the normal movement of the patient during sleep or when awake will tend to displace the catheter tubing. In addition the normal flow of blood in the vessel could tend to force the catheter tube from the patient's vessel. Using tapes, dressings and the like to secure the catheter tubing to the patient causes discomfort to the patient after a period of time due to anhydrosis which is a condition of the skin as a consequence of trapping moisture between the tape and the skin. Similarly, adhesive tapes tend to have less flexibility than the skin and as a result are -physically uncomfortable.

In an effort to overcome the problems of suturing the catheter tubing near the entry site, a suturing sleeve with a pair of ears has been tried. Such a sleeve is able to be coaxially placed over and axially slid along the catheter tube to a position adjacent to entry site. Once the sleeve is so positioned, it can be sutured to the patient and the suture can also be used to bind the catheter tube relative to the sleeve. There has been no permanent way to secure the sleeve to the tube. Efforts to wrap the suture around the tube often result in kinking, pinching or collapsing the tube. Moreover, there is concern about the process of threading the catheter tube through the sleeve since the additional handling of the catheter tube can destroy the sterility. Another problem with such sleeves is that they require placement before insertion of the catheter tube into the patient as they completely circumscribed catheter tube.

The problems, difficulties and complications of the described suturing arrangements lack a compact locking suture tab with simple, inexpensive and reliable components While such a suture tab is needed, one that can be easily and conveniently attached has been unavailable. The method of making such a suture tab has also been unknown.

SUMMARY OF THE INVENTION

In the preferred form of the invention a suture tab comprises a body with a first end and a second and a first part on the first end and a second part on the second end. The body has an inside surface and an outside surface integral therewith. The first part extends from the first end to the second part forming a line therebetween and the second part extends from the line to the second end. A plurality of openings is located about the first part and each of the openings pass generally through the body from the inside to the outside surface. Adhesion means is preferably attached to a section of the inside of the body first and second parts so they may be juxtaposed when the first and second parts are folded along the line therebetween.

The preferred suture tab may include the plurality of openings disposed through the first part on another section thereof apart from the adhesion means. The body includes a reinforcement which is a thicker area protruding from the outside surface of the first part. Ears on the first part reinforcement contain the openings and the ears are adjacent a pair of opposite edges, each of which defines an elongate dimension of the body so that at least one ear is near one edge whereby the body openings can be used to secure the tab. Preferably at least two ears are disposed near each edge. At least one ear may be near each edge and also near the line between the first and second parts.

The adhesion means is a double faced tape in the preferred embodiment and may include a releasable covering for protecting an adhesive facing prior to use. The first end has a tongue for handling and the releasable covering extends beyond the double faced tape in generally parallel coextensive relation to the tongue. The tape has a foam layer between the double faced thereof. The body is molded of a polymeric substance.

A suture tab and catheter assembly comprising a body with first and second ends and first and second parts on the first end second ends. The body has inside and outside integral surfaces The first part extends from the first end to the second part forming a line therebetween and the second part extends from line to the second end. A plurality of openings are in first part where each opening located about the first part passes generally through the body from the inside to the outside surface. The preferred catheter assembly includes a tube for placement in a lumen of a vessel or artery and at least a fluid connection thereto.

Adhesion means is attached to a section of the inside of the body first and second parts for placement in juxtaposition about and permanent attachment to the tubing upon folding of the first and second parts along the line therebetween. The tubing may be a multilumen structure with at least a fluid connection for each lumen. The plurality of openings are disposed through the first part on another section thereof apart from the adhesion means. The body includes a reinforcement being a thicker area protruding from the outside surface and ears are preferably a part of the reinforcement and contain the openings. At least a pair of opposite edges define an elongate dimension of the body and one ear is near one edge whereby the body openings can be used to secure the tab. Two ears are disposed near each edge and at least one ear is also near the line between the first and second parts.

The adhesion means is a double faced tape with a releasable covering for protecting an adhesive facing prior to use. The double faced tape has a foam layer between the double faced thereof.

The invention also includes a method for attaching a suture tab to a catheter tube with the steps of providing a suture tab having a body with first and second ends and first and second parts on the first and second ends. Inside and outside major surfaces are surrounded by an edge. Locating a plurality of openings passing through the body from one major surface to the other is another step of the method. Positioning an adhesive member on the inside major surface adhered to the first and second parts so that openings are located in another portion of the first part is a further step. Placing the body outside major surface against the patient with the adhesive member exposed to receive a catheter tube transversely thereacross and folding the body approximately in half so the outside surface of the second part is away from the patient and the inside surface carrying the adhesive member is juxtaposed with the adhesive member adhered to the catheter tube and itself is the last step of the preferred method.

The method may include the additional steps of using a double faced foam tape as the adhesive member, having a protective releasable covering overlying a face of the tape away from the inside surface and removing the releasable covering from the face prior to adhering the catheter tube to the face of the adhesive member. The added step of providing ears near the edge about the first part as the portion for the openings. The method may have the added step of suturing the suture tab to the patient by sewing through the openings.

DETAILED DESCRIPTION OF THE DRAWING

Figure 1:
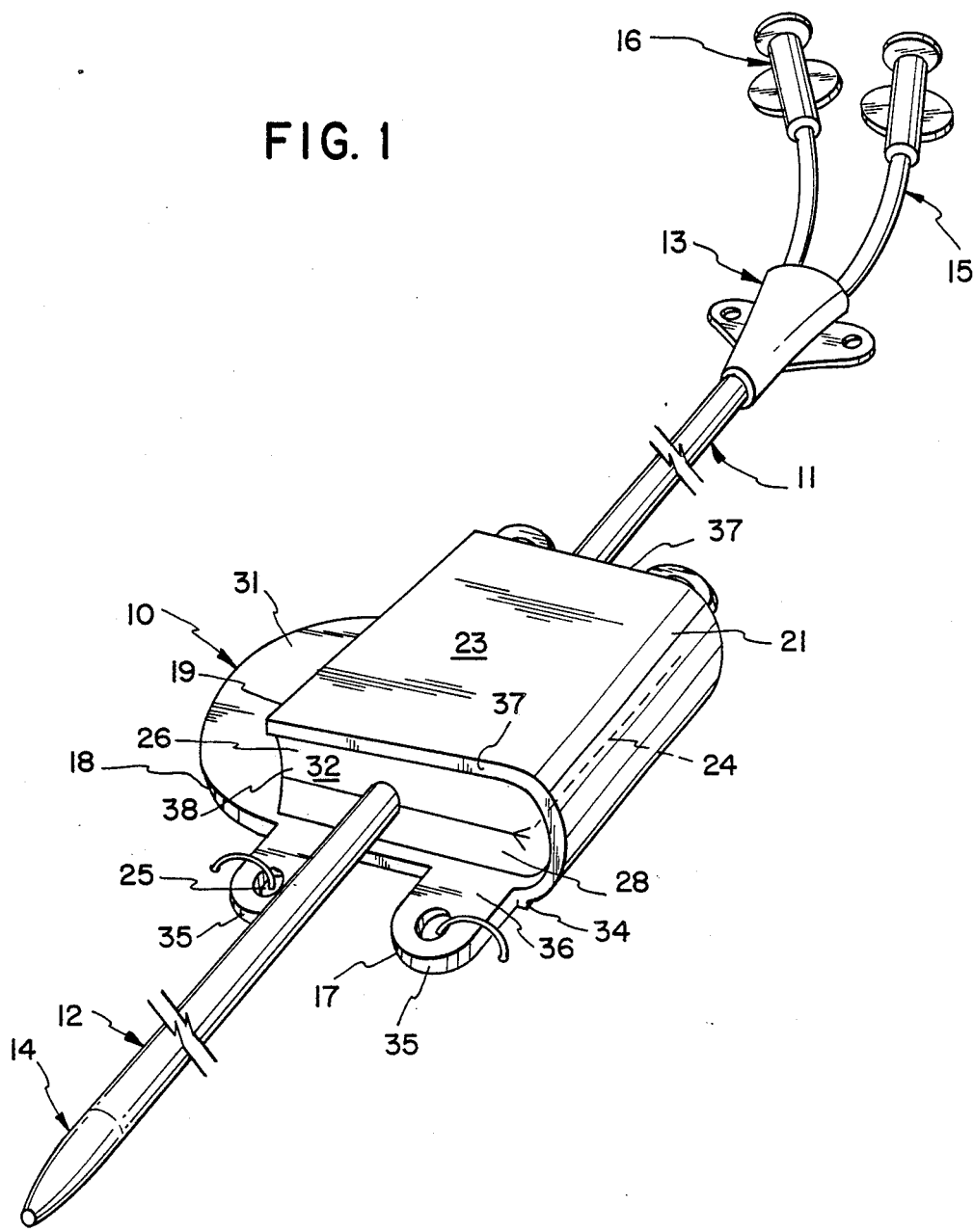
FIG. 1 is a perspective view of the preferred embodiment of a suture tab permanently attached to a catheter assembly.

While this invention is satisfied by embodiments in many different forms, there is shown in the drawings and will herein be described in detail a preferred embodiment of the invention, with the understanding that the present disclosure is to be considered as exemplary of the principles of the invention end is not intended to limit the invention to the embodiment illustrated. The scope of the invention will be measured by the appended claims and their equivalents.

FIG. 1 is the perspective view illustrating the overall appearance of the preferred embodiment of a suture tab 10 used in combination with a catheter assembly 11. The catheter assembly 11 includes a catheter 12 and its adapter 13. The catheter 12 is a flexible polymeric thin wall tube extruded from material such as polyurethane. A tapered tip 14 is used on the catheter 12 to ease insertion with an introducer technique. The catheter 12 is connected for fluid communication by extension tubes 15 having connection fittings 16.

Figure 2:
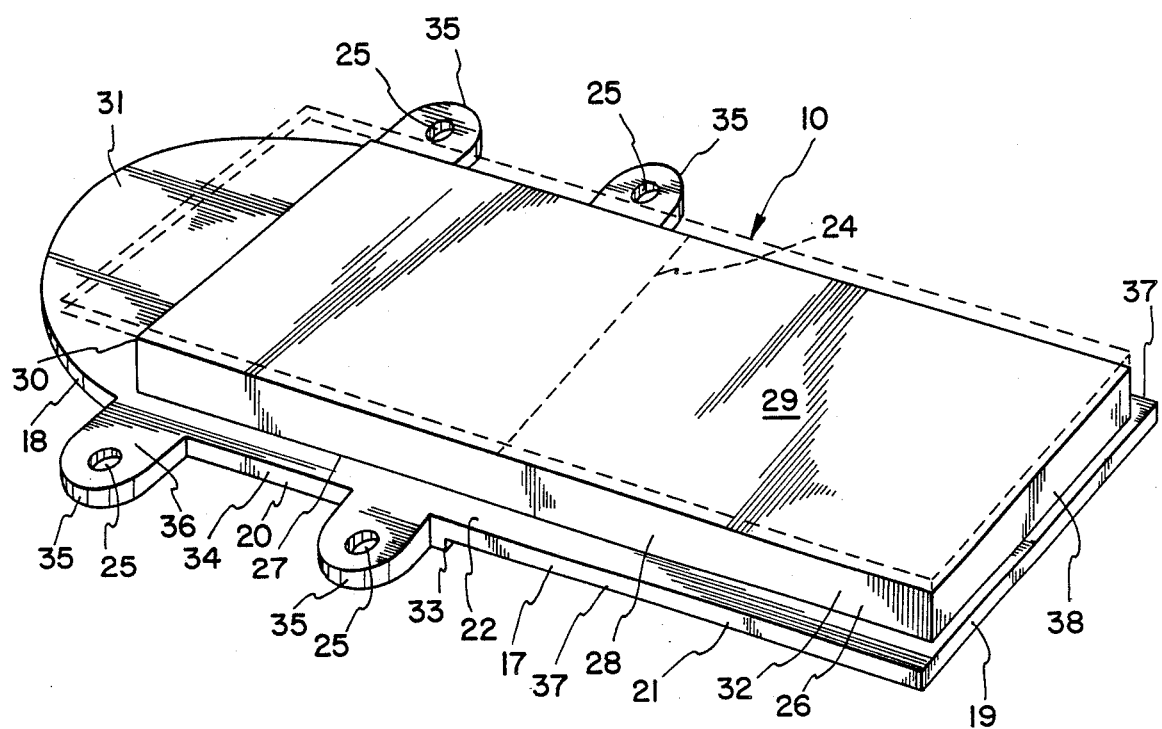
FIG. 2 is a perspective view of the preferred embodiment of a suture tab shown before it is folded about the catheter assembly.

The suture tab 10 has a body 17 with a first end 18 and a second end 19 and a first part 20 on the first end 18 and a second part 21 on the second end 19. The body 17 includes an inside major surface 22 and an outside major surface 23 integral therewith as shown in FIG. 2. The first part 20 extends from the first end 18 to the second part 21 forming a line 24 therebetween and the second part 21 extends from the line 24 adjacent to the first part to the second end 19. The body 17 preferably has a plurality of openings 25 in first part 20 in which each of the openings 25 passes through the body 17 from the inside major surface 22 to the outside major surface 23. The openings 25 are located about the first part 20 of the body 17.

Adhesion means 26, in the preferred embodiment, is attached to a section 27 of the inside major surface 22 of the first and second parts 20 and 21. The adhesion means 26 is provided for permanently holding in juxtaposition the first and second parts 20 and 21 when they are folded along the line 24 therebetween. That is to explain that the body 17 may be folded about the line 24 and the adhesion means 26 sticks or adheres to itself permanently maintaining the body 17 in the folded condition such as is illustrated in FIG. 1.

The adhesion means 26 is most preferably a double faced tape 28. As shown in FIG. 2 the tape 28 includes a releasable covering 29 for protecting an adhesive facing 30 prior to use. To facilitate application of the suture tab 10 to the catheter assembly 11, the first end 18 has a tongue 31 for handling and the releasable covering 29 extends beyond the double faced tape 28 in generally parallel coextensive relation to the tongue 31. The tongue 31 and the extended releasable covering 29 may be easily grasped and pulled apart to expose the adhesion means 26. The double faced tape 28 may in the preferred construction have a foam layer 32 between the double adhesive faced tape 28 thereof. Therefore, in use, the foam layer 32 acts to cushion and surround the catheter 12 preventing distortion or collapse of the lumen through the catheter 12 while providing permanent attachment. The foam layer 32 maintains the tongue 31 and the releasable covering 29 in spaced generally parallel coextensive relation. The adhesive used is selected for its ability to adhere to the polymeric material of the catheter 12 which in the preferred embodiment is polyurethane.

The plurality of openings 25 is preferably disposed through the first part 20 on another section 36 thereof apart from the adhesion means 26 so they may be used to suture the body 17 first pert 20 to the patient. Specifically, the suture is sewn to the patient's skin by loops of suture as illustrated in FIG. 1 thus securing the outside major surface 23 of the first part 20 against the skin. The body 17 includes a reinforcement 33 being a thicker area 34 which protrudes from the outside major surface 23 of the first part 20. The thicker area 34 extends into the other section 36 that has the openings 25. The first part 20 of the body 17 includes ears 35 in the other section 36; the ears 35 contain the openings 25 and are part of the reinforcement 33. As seen in FIG. 1 the ears 35 provide clear and convenient access to the openings 25 so that there is no obstruction which would interfere with suturing.

The body 17 has at least a pair of opposite edges 37, each of which define an elongate dimension of the body 17 and the ears 35 ere adjacent the edges 37 so that at least one ear 35 is near one edge 37 whereby the openings 25 can, as explained, be easily used to secure the suture tab 10. In the preferred embodiment of the invention as illustrated in FIGS. 1 and 2, at least two ears 35 are disposed near each edge 37 and one ear 35 is near one edge 37 and is also near the line 24 between the first and second parts 20 and 21.

The suture tab 10 has its body 17 made of a polymeric substance and body 17 is preferably molded to provide the reinforcement 33 of the thicker area 34 and the ears 35. A stamped or die cut body 17 would be less costly and might be serviceable even if the increased thickness was missing. Similarly, a die cut or stamped body 17 of thicker material with a living hinge positioned at the line 24 between the first and second parts 20 and 21 could function adequately.

A suture tab 10 and catheter assembly 11 are shown in perspective in FIG. 1 as a combination. Lengthy multilumen catheters are, as explained in the background, needed for critically ill patients where the catheter 12 frequently remains in the patient for extended periods. A device and technique which permits the suture tab 10 to be permanently secured to the catheter 12 at any place along the catheter 12 is illustrated in FIG. 2 prior to placement. In particular, the releasable covering 29 is removed and adhesive on the foam layer 32 is positioned so the catheter 12 traverses the suture tab 10 when the outside major surface 23 of the first part 20 is adjacent the body 17. The tongue 31 is there to aid in removal of the releasable covering 29 and in placement of the suture tab 10. Thereafter the adhesion means 26, attached to section 27 of the inside of the body 17 first and second parts 20 and 21, is placed in juxtaposition about the catheter 12 for permanent attachment to the catheter 12 as the first and second parts 20 and 21 are folded along the line 24.

The preferred catheter assembly 11 is a multilumen structure and there is at least a fluid connection for each lumen in the structure. The fluid connection has extension tubes 15 end connection fitting 16 on each as shown in FIG. 1. The adapter 13 is molded around the extension tubes 15 and the multilumen catheter 12 forming fluid tight multilumen assembly.

The preferred method for attaching the suture tab 10 to the catheter 12 includes several steps. Providing the suture tab 10 having body 17 with first end 18 and second end 19 and first part 20 on first end 18 and second part 21 on second end 19. The body 17 includes inside and outside major surfaces 22 and 23 surrounded by edge 37. The step of locating the plurality of openings 25 in the other section 36 or portion of first part 20 so the openings 25 pass through the body 17 from one major surface to the other is another step in the method. Positioning an adhesive member 38 or double faced tape 28 on inside major surface 22 adhered to first and second parts 20 and 21 so that openings 25 are located in another section 36 of first part 20 permits access to openings 25 for suturing.

To apply suture tab 10 to catheter assembly 11 the step of placing the body 17 outside major surface 23 against the patient with adhesive member 38 exposed to transversely receive catheter 12 thereacross is performed. The releasable covering 29 is removed to expose adhesion means 26. To secure catheter 12 the additional step of folding the body 17 approximately in half so outside major surface 23 of second part 21 is away from the patient and inside major surface 22 carrying the adhesive member 38 is juxtaposed with adhesive member 38 adhered to itself and catheter 12 is practiced by the medic or practioner.

Additional steps of using double faced tape 28 as the adhesive member 38, having protective releasable covering 29 overlying facing 30 of the tape 28 away from the inside major surface 22 and removing the releasable covering 29 from the adhesive facing 30 prior to adhering the catheter 12 to the facing 30 of adhesive member 38 simplify the construction and application of the invention. A further step of provides ears 35 near edge 37 about first part 20 and in the other section 36 of the openings 25. The method also includes the step of suturing the suture tab 10 to the patient by sewing through openings 25.

Those skilled in the art will appreciate that the body 17 may be modified as explained and that the steps of the method may be reordered. Changes in the materials described, the configuration of the preferred embodiment mentioned and the particular shape of the combined suture tab 10 and catheter assembly 11 disclosed may be made without departing from the scope of the invention covered by the claims which follow.

What is claimed is:

1. A suture tab comprising:
  a body with a first end and a second end and a first part on the first end and a second part on the second end, the body having an inside surface and an outside surface integral therewith, the first part extending from the first end to the second part and forming a fold line between the first and second parts, the second part extending from the fold line to the second end, the body having a plurality of openings in the first part each of the openings generally being through the body from the inside surface to the outside surface and located about the first part; and
  adhesion means attached to a section of the inside surface of the body first and second parts for placement in juxtaposition when the first and second parts are folded along the fold line therebetween and wherein the plurality of openings is on another section apart from the adhesion means.

2. The suture tab of claim 1 wherein the body includes a reinforcement being a thicker area protruding from the outside surface of the first part.

3. The suture tab of claim 2 wherein the body includes ears on the first part and as part of the reinforcement for containing the openings.

4. The suture tab of claim 3 wherein the body has at least a pair of opposite edges, each of which defines an elongate dimension of the body wherein and the ears are adjacent the edges so that at least one ear is near one edge where by the body openings are used to secure the tab.

5. The suture tab of claim 4 wherein at least two ears are disposed near each edge.

6. The suture tab of claim 5 wherein at least one ear near each edge is also near the line between the first and second parts.

7. The suture tab of claim 1 wherein the adhesion means is a double faced adhesive tape.

8. The suture tab of claim 7 wherein the tape includes a releasable covering for protecting an adhesive facing prior to use.

9. The suture tab of claim 8 wherein the first end has a tongue for handling and the releasable covering extends beyond the double faced tape in generally parallel coextensive relation to the tongue 10. The suture tab of claim 9 wherein the first end has a tongue for handling and the releasable covering extends beyond the double faced tape in spaced generally parallel coextensive relation to the tongue.

11. The suture tab of claim 6 wherein the double faced adhesive tape has a foam layer between double faces thereof.

12. The suture tab of claim 11 wherein the tape includes a releasable covering for protecting an adhesive facing prior to use.

13. The suture tab of claim 1 wherein the body is made of a polymeric substance.

14. The suture tab of claim 13 wherein the polymeric substance is molded to make the body.

15. A suture tab and catheter assembly comprising:
a body with a first end and a second end and a first part on the first end and a second part on the second end, the body having an inside surface and an outside surface integral therewith, the first part extending from the first end to the second part and forming a fold line between the first and second parts and the second part extending from the fold line to the second end, the body having a plurality of openings in the first part each of the openings generally being through the body from the inside surface to the outside surface and located about the first part;
a catheter assembly including a tube for placement in a lumen of a vessel or artery and at least a fluid connection thereto; and
adhesion means attached to a section of the inside surface of the body first and second parts for placement in juxtaposition about the tube for attachment to the tube when the first and second parts are folded along the fold line therebetween and wherein the plurality of openings is on another section apart from the adhesion means.

16. The suture tab and catheter assembly of claim 15 wherein the tubing is a multilumen structure.

17. The suture tab and catheter assembly of claim 16 wherein therein is at least a fluid connection for each lumen in the structure.

18. The suture tab and catheter assembly of claim 17 wherein the polymeric substance is molded to make the body.

19. The suture tab and catheter assembly of claim 15 wherein the body includes a reinforcement being a thicker area protruding from the outside surface of the first part.

20. The suture tab and catheter assembly of claim 19 wherein the body includes ears on the first part and is part of the reinforcement for containing the openings.

21. The suture tab and catheter assembly of claim 20 wherein the body has at least a pair of opposite edges, each of which define an elongate dimension of the body and the ears ere adjacent the edges so that at least one ear is near one edge where by the body openings are used to secure the tab.

22. The suture tab and catheter assembly of claim 21 wherein at least two ears are disposed near each edge.

23. The suture tab and catheter assembly of claim 22 wherein at least one ear near each edge is also near the line between the first and second parts.

24. The suture tab and catheter assembly of claim 15 wherein the adhesion means is a double faced adhesive tape.

25. The suture tab and catheter assembly of claim 24 wherein the tape includes a releasable covering for protecting an adhesive facing prior to use.

26. The suture tab and catheter assembly of claim 25 wherein the first end has a tongue for handling and the releasable covering extends beyond the double faced tape in generally parallel coextensive relation to the tongue.

27. The suture tab and catheter assembly of claim 24 wherein the double faced adhesive tape has a foam layer between the double faced thereof.

28. The suture tab and catheter assembly of claim 27 wherein the tape includes a releasable covering for protecting an adhesive facing prior to use 29. The suture tab and catheter assembly of claim 25 wherein the first end has a tongue for handling and the releasable covering extends beyond the double faced tape in spaced generally parallel coextensive relation to the tongue.

30. The suture tab and catheter assembly of claim 15 wherein the body is made of a polymeric substance.

* * * * *